United States Patent [19]

Zuk et al.

[11] 4,435,504

[45] Mar. 6, 1984

[54] IMMUNOCHROMATOGRAPHIC ASSAY WITH SUPPORT HAVING BOUND "MIP" AND SECOND ENZYME

[75] Inventors: Robert F. Zuk, Menlo Park; David J. Litman, Mountain View, both of Calif.

[73] Assignee: Syva Company, Palo Alto, Calif.

[21] Appl. No.: 398,505

[22] Filed: Jul. 15, 1982

[51] Int. Cl.³ .................... G01N 33/54; G01N 33/52; G01N 31/08; G01N 33/58

[52] U.S. Cl. .................... 435/7; 210/658; 422/56; 435/4; 435/25; 435/28; 435/805; 436/162; 436/514; 436/530; 436/541; 436/810; 436/815

[58] Field of Search .............. 436/514, 530, 810, 541; 435/7, 4, 25, 28, 805; 422/56; 210/658

[56] References Cited

U.S. PATENT DOCUMENTS

| | | | |
|---|---|---|---|
| 4,168,146 | 9/1979 | Grubb | 436/805 |
| 4,205,058 | 5/1980 | Wagner | 210/658 X |
| 4,298,688 | 11/1981 | Kallies | 435/28 |

OTHER PUBLICATIONS

C. Glad et al., Anal. Biochem., 85, 180–187 (1978).
C. Glad et al., Anal. Biochem., 116, 335–340 (Sep. 15, 1981).

*Primary Examiner*—Sidney Marantz
*Attorney, Agent, or Firm*—Bertram I. Rowland

[57] ABSTRACT

Chromatographic immunoassay employing a specific binding pair member and a label conjugate which delineates a border whose distance from one end of the chromatograph relates to the amount of analyte present. By combining the label conjugate and sample in a solution and immunochromatographing the solution, or employing a combination of enzymes, one enzyme being the label and the other enzyme affixed to the chromatographic support, the position of the border defined by the label can be related to the amount of analyte in the sample solution.

Preferably, an immunochromatograph is employed having both a specific binding pair member and an enzyme affixed to the support. A sample is chromatographed and the amount of analyte is determined by (1) contacting the chromatograph with a second enzyme conjugated with a specific binding pair member which binds to the chromatograph in proportion to the amount of analyte bound to the chromatograph, or (2) including the second enzyme conjugate with said sample, resulting in a defined border related to the amount of analyte in the sample. The two enzymes are related in that the substrate of one is the product of the other, so that upon contact of the chromatograph with appropriate reagents, a detectable signal develops which permits detection of the border to which the analyte traveled. This distance can be related to the amount of analyte present in the sample.

12 Claims, No Drawings

IMMUNOCHROMATOGRAPHIC ASSAY WITH SUPPORT HAVING BOUND "MIP" AND SECOND ENZYME

BACKGROUND OF THE INVENTION

1. Field of the Invention

The field of competitive protein binding assays or specific binding assays has greatly expanded, as its importance in the diagnostic field has become recognized. The ability to be able to detect a specific compound and measure the compound quantitatively has permitted the monitoring of the administration of a wide variety of drugs, the determination of an imbalance in a wide variety of hormones, the quantitation of physiologicaly active proteins, and the diagnosis of the presence of a pathogen. The different techniques have been distinguished in requiring or not requiring separation steps, the nature of the signal developed by a label, the development of the signal in a solution or on a surface and the manner of measurement for a quantitative determination.

In developing an assay, there are a number of considerations in devising the reagents and protocol. One consideration is the degree of sophistication of the individual performing the assay. There are many situations where it is desirable to have a relatively untrained individual to be able to carry out an assay and obtain reasonably quantitative results. In these situations, it is desirable that the assay be reasonably free from interference by materials in the sample, be relatively free of fluctuations with changes in environmental conditions and provide for easy measurement. Also, washings can be a source of error, either because of inadequate washing, leaving non-specific binding material, or by reversing specific binding.

2. Description of the Prior Art

U.S. Pat. No. 4,168,146 describes an immunoassay employing immunochromatography with antigens followed by contacting the immunochromatograph with an aqueous solution containing labeled antibodies. U.S. Pat. No. 4,233,402 describes a homogeneous assay method employing a combination of enzymes, where the substrate of one enzyme is the product of another. Enhanced production of the product is related to the amount of analyte in the assay medium. U.S. Pat. No. 4,275,149 describes the use of particles where combinations of enzymes may be employed, where the presence of the particles enhances the interaction between two enzymes, where the product of one enzyme is the substrate of the other. Enhanced production of the final product due to the presence of the two enzymes bound to the particle as a result of binding of specific binding pair members is related to the amount of analyte in the assay medium.

SUMMARY OF THE INVENTION

Novel immunochromatographic methods are provided for detecting an analyte where a quantitative determination may be readily made without special equipment. The analyte is immunochromatographed on a bibulous carrier in the presence or absence of a labeled conjugate where the label is a member of an enzymatic signal producing system, which includes one or more enzymes. After chromatographing the analyte, if the enzyme conjugate was not included in the sample, the chromatograph is contacted with a labeled specific binding pair member which binds to the chromatograph in relation to the distance travelled by the analyte. By providing appropriate reagents, in the case of two enzymes where the substrate of one enzyme is the product of the other enzyme, a final product is produced which provides for a detectable signal, where the distance traveled by the analyte may be defined, which distance is related to the amount of analyte in the sample.

DESCRIPTION OF THE SPECIFIC EMBODIMENTS

Methods and compositions are provided for use in determining the presence of an analyte in a sample. The method involves an immunochromatograph where a border is developed intermediate the ends of the immunochromatograph, where the distance of the border from one end of the immunochromatograph is related to the amount of analyte in a sample.

While various protocols may be employed, invariably, the immunochromatograph will be contacted at one end with a sample solution and the solution will travel up the immunochromatograph. Various techniques may then be used by combining one or more reagents which provide a clear delineation between the region to which the analyte is bound and the region free of analyte. The techniques may involve a single reagent or a combination of reagents, in order to enhance the clear delineation between the region where analyte is bound from the region where it is absent. This may involve, in the analyte bound or the analyte free region, providing a detectable signal throughout one or the other region, resulting in two distinct regions, or developing a distinctive border between the two regions. By appropriate choice of the reagents and materials employed, one can provide for production of signal in either of the regions, analyte bound or analyte free, or primarily at the border between the two regions. By employing the subject protocols and reagents, wash steps are minimized and adventitious interference with a quantitative result is substantially avoided.

In performing the subject assay, an analyte is measured which is a member of a specific binding pair consisting of ligand and receptor. The ligand and receptor are related in that the receptor specifically binds to the polar and spatial organization of the ligand, being able to distinguish the ligand from other compounds having similar characteristics. An immunochromatograph is employed which is characterized by having one of the members of the specific binding pair non-diffusely bound to a bibulous support which allows for movement of a liquid by capillarity through the support. In addition to the specific binding pair member, there will also be an enzyme member of a signal producing system. The signal producing system involves reagents which allow for an accurate determination of the region in which the analyte is bound or absent, while minimizing washing or other steps to reduce non-specific binding.

In carrying out the assay, the immunochromatograph is contacted with the sample containing solution. The sample containing solution may also include a member of the signal producing system bound to a specific binding pair member. Alternatively, or in addition, the signal producing members other than any signal producing members initially part of the immunochromatograph may be added in one or more successive solutions. The sample will traverse a region of the immunochromatograph by elution or solvent transport, and, in some protocols, a conjugate of a specific binding pair member and a signal producing system member will also traverse the immunochromatograph.

To further explain the subject invention, in the subsequent description of the subject invention, the following definitions will be used.

DEFINITIONS

Analyte—The compound or composition to be measured, which may be a ligand, which is mono- or polyepitopic, antigenic or haptenic, a single or plurality of compounds which share at least one common epitopic site or a receptor.

Specific Binding Pair ("Mip")—Two different molecules, where one of the molecules has an area on the surface or in a cavity which specifically binds to a particular spatial and polar organization of the other molecule. The members of the specific binding pair are referred to as ligand and receptor ("anti-ligand"). For the most part, the receptor will be an antibody and the ligand will serve as an antigen or hapten and to that extent are members of an immunological pair. Therefore, each of the members may be referred to as a mip, it being understood that "mip" is intended to include all ligands and all receptors.

Ligand—Any organic compound for which a receptor naturally exists or can be prepared.

Receptor ("Anti-Ligand")—Any compound or composition capable of recognizing a particular spatial and polar organization of a molecule, i.e. epitopic site. Illustrative receptors include naturally occuring receptors, e.g. thyroxin binding globulin, antibodies, enzymes, FAB fragments, lectins and the like.

Label—The label may be any molecule conjugated to another molecule or support and where two molecules are involved is arbitrarily chosen as to which molecule is the label. In the subject invention, the labels will be a mip which is conjugated to a support or a member of the signal producing system that is conjugated to a support or a mip.

Signal Producing System—The signal producing system may have one or more components, at least one component being conjugated to a mip. The signal producing system produces a measureable signal which is detectable by external means, normally by measurement of the electromagnetic radiation, desirably by visual examination. For the most part, the signal producing system involves chromophores and enzymes, where chromophores include dyes which absorb light in the ultraviolet or visible region, phosphors, fluorescers and chemiluminescers.

Immunochromatograph—The immunochromatograph has a plurality of mips, either ligand or receptor, bound in an region to a bibulous support which allows for the movement of a liquid across the region with transport of the analyte and, as appropriate, any members of the signal producing system. The mips are non-diffusively bound to the support, either covalently or non-covalently. In addition, one or more members of the signal producing system may be non-diffusively bound to the bibulous support, either covalently or non-covalently.

METHOD

The subject method is carried out on a bibulous support involving a stationary solid phase and a moving liquid phase. The stationary solid phase may be contacted with a plurality of reagents in sequence in a number of different solutions, normally omitting wash steps between contacting with subsequent reagent compositions.

The region in which the mip is non-diffusively bound to the bibulous support is referred to as the immunosorbing zone. The analyte from the sample will traverse this zone being carried along with a solvent whose front crosses the zone. The analyte, which is the homologous or reciprocal mip to the mip bound to the support, becomes bound to the support through the intermediacy of mip complex formation. The signal producing system provides the manner in which the area in the immunosorbing zone to which the analyte is bound may be distinguished from the area in which it is absent, so that the distance from a predetermined point on the immunochromatograph is a measure of the amount of analyte in the sample.

The incremental movement of the sample through the immunosorbing zone results from dissolving the sample in an appropriate solvent and the transport of the solution through the immunosorbing zone due to capillarity.

The solvent will normally be an aqueous medium, which may be up to about 40 weight percent of other polar solvents, particularly oxygenated solvents of from 1 to 6, more usually of from 1 to 4 carbon atoms, including alcohols, ethers and the like. Usually, the cosolvents will be present in less than about 20 weight percent.

The pH for the medium will usually be in the range of 4–11, more usually 5–10 and preferably in the range of about 6.5–9.5. The pH is chosen to maintain a significant level of binding affinity of the mips. Various buffers may be used to achieve the desired pH and maintain the pH during the elution. Illustrative buffers include borate, phosphate, carbonate, tris, barbital and the like. The particular buffer employed is not critical to this invention, but in individual assays, one buffer may be preferred over another.

Desirably, from about 0.05 to 0.5 wt. % of a non-ionic detergent is included with the sample. Various polyoxyalkylene compounds may be employed of from about 200 to 20,000 daltons.

Moderate, and desirably substantially constant, temperatures are normally employed for carrying out the assay. The temperatures for the elution and production of a detectable signal will generally be in the range of about 10°–50° C., more usually in the range of about 15°–50° C., and frequently will be ambient temperatures, that is, about 15°–25° C.

The concentration of analyte which may be assayed will generally vary from about $10^{-4}$ to about $10^{-15}$ M, more usually from about $10^{-6}$ to $10^{-14}$ M. Considerations, such as whether the assay is qualitative, semi-qualitative, or quantitative, the particular detection technique; the concentration of the analyte of interest; and the protocol will normally determine the concentration of the other reagents.

While the concentrations of many of the various reagents in the sample and reagent solutions will generally be determined by the concentration range of interest of the analyte, the final concentration of each of the reagents will normally be determined empirically to optimize the sensitivity of the assay over the range of interest. However, with certain protocols, individual reagents may be used in substantial excess without detrimentally affecting the sensitivity of the assay.

The size of the immunosorbing zone need have no upper limit, except for practical considerations. Since, for the most part, low concentrations are being assayed, the width of the immunoabsorbing zone will tend to be relatively narrow, so that the analyte may traverse a reasonable distance and provide for reasonable differentiation over the concentration of interest. Generally, the width of the strip will not be less than about 0.2 mm and not more than about 2 cm, generally ranging from about 5 mm to 20 mm, preferably from about 5 mm to 15 mm. A plurality of individual strips may be used. Instead of strips, cylinders may be employed, e.g. a rod.

The length of the immunoabsorbing zone will be desirably at least about 2 to 10 times the width, usually at least about 2 mm, more usually at least about 10 mm, preferably at least about 23 mm, and not more than about 12 cm, usually not more than about 10 cm, preferably from about 5 to 10 cm. The distance traversed is a factor in the time required for the assay, which will be taken into account with the other factors affecting the time required for the assay.

Other reagents which are members of the signal producing system may vary widely in concentration depending upon the particular protocol and their role in signal production. In a "true" competitive situation between a labeled mip and the analyte, usually the labeled mip will not exceed 10 times the maximum concentration of interest of the analyte and will not be less than about 0.5 times the minimum concentration of interest. In most other situations, the amount of the other reagents involved in mip complex formation may be present in an amount substantially less than the binding equivalent of analyte or in substantial excess to the binding equivalent of analyte. Therefore, no simple relationship can be provided.

In carrying out the assay, the protocol will normally involve dissolving the sample into the eluting solvent. The sample may be derived from a wide variety of sources, such as physiologic fluids, illustrated by blood, serum, plasma, urine, ocular lens fluid, spinal fluid, etc., chemical processing streams, food, pesticides, pollutants, etc.

One end of the chromatograph will then be contacted with the eluting sample containing solvent, which will normally be a buffered aqueous medium which may contain one or more members of the signal producing system. Where a member of the signal producing system is present, at least one member will be conjugated to a mip to provide a mip-label conjugate.

Sufficient time will be allowed for the solvent front to completely traverse the immunosorbing zone. The zone has sufficient mip to insure that all of the analyte becomes bound in said zone without exhausting the mip bound in the zone.

The labeled mip may be employed in three different ways, two of the ways involving the labeled mip being present in the eluting solvent and the third way involving the labeled mip being present in a reagent solution used after elution of the sample. The two ways involving the eluting solvent are either where the mip-label traverses the immunosorbing zone concurrently with the analyte, so as to actually compete with the analyte for available binding sites; or, where the mip-label does not have an apparent competition and primarily binds in a zone immediately beyond the zone in which the analyte has bound. In one instance, one obtains a zone extending from the initial line of contact of the sample containing solvent with the immunochromatograph, while in the other situation, a border results distinguishing between the zone in which the analyte is bound and the zone which is analyte free.

In the third way, where one has antigenic analytes, the method can involve an initial contact with the sample, where the sample traverses the immunosorbing zone, followed by immersing the immunosorbing zone in a sample containing labeled mip, which binds to the antigen. This assay is conventionally referred to as a sandwich assay. Of course, where a hapten is involved, one can provide for a fixed amount of a polyligand, that is, the ligand can be polymerized or conjugated to a hub nucleus, so as to provide for a plurality of determinant sites common to both the haptenic analyte and the polyligand. In effect, one produces an antigen where the extent of travel of the synthetic antigen will be related to the amount of analyte in the sample. When the immunochromatograph is contacted substantially uniformly, e.g., immersing, spraying, etc., with a solution containing labeled mip, the labeled mip will bind to the available determinant sites of the antigen, resulting in a detectable signal defining a region related to the amount of analyte in the sample.

Rather than employ an antigen, which acts as a bridge between two antibodies, one can employ one mip in the solution with the reciprocal mip on the immunochromatograph. After allowing the analyte to traverse the immunosorbing zone, the immunosorbing zone is contacted, substantially uniformly, e.g., immersing, spraying, etc., with a solution of labeled mip. The labeled mip is complementary to the mip bound to the immunoabsorbing zone, so that the labeled mip will bind to available binding sites defining the region in the immunoabsorbing zone free of analyte. In this way, the distance the analyte has traversed is indicated by the absence of an observable signal in the region containing the analyte, and the border is defined by the presence of the signal in the region free of the analyte.

Depending upon the particular protocols, washings may be useful or desirable or may be avoided all together. The subject invention permits the elimination of washing steps. Preferred protocols are those which provide for a minimal number of steps with minimal possibility of operator error. Therefore, the devised protocols should minimize measurement steps where the results are responsive to errors in measurement.

Where the immunochromatograph is not standardized to the extent that variations in conditions may change the distance the analyte traverses, a standard sample can be provided having a known amount of analyte. The analyte sample and the standard can be run at the same time, and a quantitative comparison can be made between the standard sample and the analyte sample. If necessary, more than one standard can be employed, so that the distance traversed can be graphed for the different concentrations and used to quantitate a particular sample.

For the most part, relatively short times are involved for the immunochromatograph. Usually, the traverse of the sample through the immunosorbing zone will take at least 30 sec and not more than 1 hour, more usually from about 1 min to 30 min. The development of the signal will generally range from 30 sec to 30 min, more usually from about 30 sec. to 5 min.

The signal producing system has at least one enzyme and may have two or more other components of the signal producing system or one or more substrates, and may also include coenzymes. Any member of the signal producing system may be employed as a label, where the presence of the label on the immunochromatograph provides for a substantial change in signal in the area of the label. Therefore, labels may include enzymes or coenzymes, but not substrates. Usually, the label will be an enzyme.

The label provides for a multiplicity of events in its vicinity by providing for enzyme turnover of a substrate. Thus, the member of the signal producing system which is used as the label will be referred to as the enzymatic signal amplifier and is limited to those members indicated above.

The individual or combination of enzyme labels may be varied widely. The product producing the detectable signal may be a dye, fluorescer or chemiluminescer, with the signal detected by visual observation, due to absorption, fluorescence, or chemiluminescence, or a spectrophotometric measurement, employing measuring absorption, reflectance, fluorescence or chemiluminescence.

For the most part the enzymes of interest will be oxidoreductases and hydrolases. A large number of enzymes of interest are set forth in U.S. Pat. No. 4,275,149. For combinations of enzymes one enzyme is non-diffusively bound to the immunochromatograph, while the other enzyme is conjugated to a mip.

After the sample has traversed the immunosorbing zone, if the label-mip conjugate was not combined with the sample, the immunosorbing zone is contacted substantially uniformly with a solution having labeled-mip conjugate and depending on the label and protocol one or more other members of the signal producing system.

In the case of an enzyme-mip conjugate the immunosorbing zone is contacted with a solution of enzyme-mip conjugate and substrate, optionally with a scavenger. In this situation, an enzyme is bound to the immunochromatograph in the immunosorbing zone, which is related to the enzyme bound to the mip, by the substrate of one being the product of the other. The enzyme-mip conjugate will normally be in an aqueous buffered solution and may be present in substantial excess of available binding sites. The pH range and buffers have been previously considered. After a sufficient time for the enzyme-mip conjugate to bind either to ligand or receptor, and for color to form, the immunochromatograph is removed from the solution.

By having the two enzymes, a step in the protocol is eliminated since the enzyme-mip conjugate and substrate may be combined in the same solution without reaction prior to contacting the immunosorbing zone.

After the enzyme-mip conjugate is bound to the immunochromatograph, by being present in the sample, the immunochromatograph is developed by immersion in a substrate solution. In this case an enzyme may or may not be bound to the immunochromatograph.

With the coenzyme label, the developer solution will usually contain one or more enzymes to provide for regeneration of the coenzyme and substrate. Since the enzymatic reaction requires the coenzyme, the enzyme and substrate may be combined as a single developer reagent without any reaction prior to contact with the immunosorbing zone.

The substrates will vary with the enzymes and are normally in substantial excess, so as not to be rate limiting (greater concentration than Km). The aqueous solution will usually be appropriately buffered for the enzyme system and may include a scavenger for the product of the enzyme which is the substrate of the other enzyme e.g. catalase for hydrogen peroxide from uricase.

The immunochromatograph is contacted with the developer solution for a sufficient time to produce sufficient detectable signal producing compound so as to define the region of the immunosorbing zone in which the analyte is bound. Once the detectable signal has been produced, the distance from one end of the chromatograph may be measured as a quantitative measure of the amount of analyte in the sample.

While some distortion may be observed at the border, in most situations the border is reasonably well defined, so that changes in concentration of factors of two or less in the $\mu$g to pg range can be detected with a wide variety of analytes. Thus, by employing an appropriate dye precursor as a substrate, the amount of an analyte can be quantitatively determined by visual observation with a single measurement (the sample) by the user and a two-step protocol which is relatively insensitive to interference.

MATERIALS

The components employed in the subject immunochromatography are: the bibulous support, the mip conjugates, (which include the mip and the label), the mip bound to the bibulous support in the immunosorbing zone, remaining members of the signal producing system, analyte, and, as appropriate, polyligand or polyvalent receptor.

ANALYTE

The ligand analytes of this invention are characterized by being monoepitopic or polyepitopic, while the receptor analytes may have a single or plurality of binding sites. The polyepitopic analytes will normally be poly (amino acids), i.e. polypeptides and proteins, polysaccharides, nucleic acids, and combinations thereof. Such combinations or assemblages include bacteria, viruses, chromosomes, genes, mitochondria, nuclei, cell membranes and the like.

For the most part, the polyepitopic ligand analytes employed in the subject invention will have a molecular weight of at least about 5,000, or usually at least about 10,000. In the poly(amino acid) category, the poly (amino acids) of interest will generally be from about 5,000 to 5,000,000 molecular weight, more usually from about 20,000 to 1,000,000 molecular weight, and among hormones of interest, about 5,000 to 60,000 molecular weight.

An extensive listing of useful ligands may be found in U.S. Pat. No. 4,275,149, the disclosure bridging columns 12 to 17, which disclosure is incorporated herein by reference.

The monoepitopic ligand analytes will generally be from about 100 to 2,000 molecular weight, more usually from about 125 to 1,000 molecular weight. The analytes of interest include drugs, metabolites, pesticides, pollutants, and the like.

A large number of analytes of interest are listed in U.S. Pat. No. 4,275,149, columns 17 and 18, which disclosure is incorporated herein by reference.

For receptor analytes, the molecular weights will generally range from about $10^4$ to $2\times10^8$, more usually from about $3\times10^4$ to $2\times10^6$. For immunoglobulins, IgA, IgD, IgE, IgG and IgM, the molecular weights will generally vary from about 160,000 to about $10^6$. Enzymes will normally vary from about 10,000 to 600,000 daltons. Natural receptors vary widely, being generally at least about 25,000 molecular weight and may be $10^6$ and higher, including such materials as avidin, thyroxine binding globulin, thyroxine binding prealbumin, transcortin, membrane surface proteins, etc.

Where a ligand is conjugated to another molecule or support, frequently the ligand will be modified to provide for a particular functional group at a particular site. This modification produces a product referred to as a ligand analog. U.S. Pat. No. 4,275,149 also has an extensive description of ligand analogs, bridging columns 18 and 19, which description is incorporated herein by reference.

Immunochromatograph

The immunochromatograph involves a bibulous support providing liquid travel through capillarity, a non-diffusively bound mip, and may also include one or more members of the signal producing system.

A wide variety of supports may be used of different dimensions, particularly thicknesses, different materials and different shapes. For the most part, the shape will be elongated, conveniently a rectangular strip. At least a portion of the strip will have a mip uniformly bound to the strip. The size of the strip will be governed to some degree by convenience in handling. Also, the immunosorbing zone must be of sufficient size to be able to accommodate all of the analyte which may be present in the concentration range of interest of the analyte. Where the protocol involves binding of both analyte and labeled mip, then the immunosorbing zone must include capacity for both the analyte and labeled mip.

A wide variety of bibulous supports may be used, which include both natural and synthetic polymeric materials, particular cellulosic materials, such as fiber containing papers, e.g. filter paper, chromatographic paper, etc., synthetic or modified natural occurring polymers, such as poly(vinyl chloride), cross-linked dextran, acrylates, etc., either used by themselves or in conjunction with a ceramic material, such as silica.

The thickness of the immunochromatograph bibulous support will generally vary from about 0.05 mm to about 2 mm, more usually being about 0.1 mm to 0.5 mm, preferably from about 0.2 mm to about 0.4 mm. The structure of the paper may be varied widely and includes fine, medium fine, medium, medium coarse and coarse. The surface may be varied widely with varying combinations of smoothness and roughness combined with hardness and softness.

The immunochromatograph may be supported by a variety of inert supports, such as Mylar, polystyrene, polyethylene, or the like. The supports can be used as a backing spaced from the immunochromatograph, edging, or other structure to enhance the mechanical integrity of the immunochromatograph.

The immunochromatograph may be coated with a wide variety of materials to provide for enhanced properties. Coatings may include protein coatings, polysaccharide coatings, sugars or the like, which are used particularly to enhance the stability of the materials conjugated to the support. These compounds may also be used for improved binding of the materials, such as the mip or signal producing system member bound to the immunochromatograph.

The immunochromatograph may be activated with reactive functionalities to provide for covalent bonding of the organic materials to be conjugated to the support. Various techniques which may be used to activate the immunochromatograph's bibulous support, including functionalization with an acyl group e.g. carbonyldiimidazole, treatment with cyanogen bromide or difunctional agents such as glutaraldehyde, succinic acid, etc. Methods for binding of a wide variety of materials to a bibulous support may be found in the literature. See for example, U.S. Pat. No. 4,168,146.

The amount of mip which is bound to the support will vary depending upon the size of the support and the amount required to bind all of the analyte and, as required, labeled mip. Generally, the amount of mip will range from about $10^{-5}$ to $10^{-14}$ moles/cm$^2$, more usually from about $10^{-7}$ to $10^{-12}$ moles/cm$^2$. The number of moles per unit area will be varied in order to insure that there is sufficient discrimination in the concentration range of interest for the distance traversed by the analyte.

In a preferred embodiment, a signal producing system member is non-diffusively bound to the bibulous support. Particularly, an enzyme is bound to the support which will interact with the labeled mip, where the label is another enzyme. The relationship of the enzymes will be discussed in the description of the signal producing system.

Both the mip and the signal producing system member may be bound to a variety of supports by adsorption, rather than covalent bonding. This will involve contacting the bibulous support with the solution containing the mip and/or signal producing member, removing the immunochromatograph from the solution, and allowing the immunochromatograph to dry. Alternatively, the solution may be applied by spraying, painting, or other technique which will provide uniformity.

Generally, relatively large sheets will be used which may then be cut to the appropriate dimensions.

Signal Producing System

The signal producing system will, for the most part, involve the production of a detectable signal involving the absorption or emission of electromagnetic radiation, particularly light in the ultraviolet and visible region, more particularly radiation having a wavelength in the range of about 400 to 800 nm. Because of the nature of the immunochromatograph, in order to have a detectable signal, it is necessary that there be a sufficient concentration of the label over a unit area. Therefore, for the most part, individual labels will not be sufficient to provide the desired sensitivity. To that extent, means must be provided for the generation of a plurality of detectable molecules associated with a single labeled mip, where the label which provides the means for such generation does not interfere with the traversing of the labeled mip, when the labeled mip traverses the immunosorbing zone. Therefore, one employs a label which produces a large number of molecules which can be detected, such as an enzyme or coenzyme. Amplification is then obtained by the presence of a single label.

An enzyme or coenzyme is employed which provides the desired amplification by producing a product, which absorbs light, e.g. a dye, or emits light upon irradiation or chemical reaction, a fluorescer, or chemiluminescer. A large number of enzymes and coenzymes for providing such products are indicated in U.S. Pat. No. 4,275,149 bridging columns 19 to 23, and U.S. Pat. No. 4,318,980, columns 10 to 14, which disclosures are incorporated herein by reference.

Of particular interest is the use of a combination of enzymes, where the enzymes are related by the product of one enzyme being the substrate of the other enzyme. In this manner, non specific interference is substantially reduced and the border between the zones containing the bound analyte and free of analyte is more effectively defined.

A number of enzyme combinations are set forth in U.S. Pat. No. 4,275,149, bridging columns 23 to 28, which combinations can find use in the subject invention. This disclosure is incorporated herein by reference.

Of particular interest are enzymes which involve the production of hydrogen peroxide and the use of the hydrogen peroxide to oxidize a dye precursor to a dye. Particular combinations include saccharide oxidases e.g. glucose and galactose oxidase, or heterocyclic oxidases, such as uricase and xanthine oxidase, coupled with an enzyme which employs the hydrogen peroxide to oxidize a dye precursor, e.g. peroxidase, microperoxidase, and cytochrome C oxidase. Additional enzyme combinations may be found in the subject matter incorporated by reference. While the above oxidoreductase combination is preferred, other enzymes may also find use such as hydrolases, transferases, and oxidoreductases other than the ones indicated above.

Illustrative coenzymes which find use include NAD[H]; NADP[H], pyndixal phosphate; FAD[H]; FMN[H], etc., usually coenzymes which combine with oxidoreductases. For a number of coenzymes involving cycling reactions see particularly U.S. Pat. No. 4,318,980.

The product of the enzyme reaction will usually be a dye or fluorescer. A large number of illustrative fluorescers are indicated in U.S. Pat. No. 4,275,149, columns 30 and 31, which disclosure is incorporated herein by reference.

By appropriate manipulation or choice of the label-mip conjugate, the receptors, the bibulous support and the conditions employed in performing the assay, two different embodiments of the subject invention can be achieved where the analyte and enzyme-mip are applied to the immunochromatograph in the same solution. In one embodiment, the region of the immunosorbing zone traversed by the analyte is observable due to production of the detectable signal substantially uniformly throughout the region in which the analyte is present. In the other embodiment, the detectable signal is primarily observable at a border related to the region in the immunosorbing zone occupied by the analyte.

The different results may be related to different binding constants, rates of travel, adsorption or the like, of the label-mip conjugate as compared to the analyte. The variations can be achieved by varying the number of mips, particularly haptenic analytes, bound to the labels, varying the binding specificity of receptors bound to the bibulous support e.g. by preparing antibodies to an immunogen having one linking group between the hapten analyte and antigen and employing a different linking group with the label-hapten analyte conjugate, varying the solvent and/or support to vary the Rf factors, or other techniques.

As a result of the use of two enzymes in the signal producing system with one enzyme as a label, a simplified protocol can be employed, also a strong detectable signal is obtained providing for accurate delineation of the front to which the analyte progressed. By having the product of the enzyme bound to the bibulous support be the substrate of the enzyme conjugated to the mip, a sharp, rapid and uniform development of the detectable signal is observed on the immunochromatograph. Furthermore, one establishes a high localized concentration of substrate for the enzyme bound to the immunochromatograph, so as to encourage the rapid deposit of the detectable signal producing compound at the surface.

Kits

As a matter of convenience, the immunochromatograph can be provided in combination with other reagents for use in assaying for an analyte. Where two enzymes are involved, the other reagents will include enzyme labeled mip, substrate for the enzyme bound to the support, any additional substrates and cofactors required by the enzymes, and the dye precursor, which provides the detectable chromophore or fluorophore. With the coenzyme label the coenzyme labeled mgs, appropriate enzyme(s) including the dye precursor will be included. In addition other additives may be included, such as stabilizers, buffers, and the like. The relative amounts of the various reagents may be varied widely, to provide for concentrations in solution of the reagents which substantially optimize the sensitivity of the assay. Particularly, the reagents may be provided as dry powders, usually lyophilized, including excipients, which on dissolution will provide for a reagent solution having the appropriate concentrations for combining with the sample.

EXPERIMENTAL

The following examples are offered by way of illustration and not by way of limitation.

The following abbreviations are used hereafter: HRP—horse radish peroxidase; NHS—N-hydroxy succinimide; EDCA—ethyl dimethylaminopropyl carbodiimide; DMF—dimethyl formamide; BSA—bovine serum albumin. Temperatures not otherwise indicated are Celsius, while parts are by weight except for mixtures of liquids which are by volume.

EXAMPLE 1

Preparation of Immunochromatograph

Antibodies to theophylline (antitheophylline) and glucose oxidase are the materials to be conjugated. A sheet of Whatman 31ET of about 550 $cm^2$ is immersed in 1.8 L pyridine, 0.2 M in carbonyldiimidazole and the mixture gently stirred for one hour at room temperature. Additional sheets may be activated in the same activating solution. Each sheet is then washed with 300 ml tetrahydrofuran and air dried with an air gun over about 20 sec. The sheet is then immersed in a solution of 500 $\mu$l of a 49 mg/ml solution of antitheophylline, 790.5 $\mu$l of a 16 mg/ml solution of glucose oxidase amine and 200 ml of buffer 0.1 M sodium phosphate, pH 7.0, 0.2 M NaCl and the mixture mildly shaken for 4 hours at room temperature. After washing with the phosphate buffer, the solution is then immersed in a 4% aqueous Dextran T10 solution to serve as a preservative, followed by blotting the sheet, freeze drying and lyophilizing.

EXAMPLE 2

Conjugation of Theophylline and HRP

Into a reaction flask was introduced 8.1 mg of 1-methyl-3-(3'-carboxypropyl)xanthine, 3.8 mg of NHS, 6.7 mg EDAC and 125 $\mu$l DMF and the mixture allowed to stand overnight at room temperature.

To four 1.3 ml samples of HRP-oxyamine (1 mg) in 0.1 M sodium carbonate, pH 9.0 was added varying amounts of the ester prepared above to provide for preparations having mole ratios of theophylline to HRP of 400; 200, and two of 100 each. Into the first reaction mixture (400 mole ratio) was added 0.217 ml of DMF and 66 µl of the above ester in 8.25 µl increments over a period of about 2 hrs. Into the second reaction mixture (200 mole ratio), 0.238 ml of DMF was added and 33 µl of the ester added incrementally in 8.25 µl increments. Into the third reaction mixture (100 mole ratio), 0.24 ml of DMF was added and 16.5 µl of the ester added in 8.2 µl increments, while in the final reaction mixture (100 mole ratio), no DMF was added, and 8.25 µl of the ester was added in 2.1 ||1 increments. During the addition, the temperature was maintained at 4°, and the mixture then allowed to stand overnight at 4°.

The reaction mixtures were then worked up by chromatography on G-25 Sephadex with standard buffer. Folin and UV spectroscopic analysis indicated theophylline/HRP ratios of 6.9, 4.0, 1.6 and 2.1, respectively.

EXAMPLE 3

Preparation of Glucose Oxidase Amine

Glucose oxidase (Sigma, E.C. 1.1.3.4) was concentrated from 360 ml to 60 ml with Amicon PM10 membrane at a pressure below 30 psi. The concentrate of glucose oxidase was dialyzed twice against 4 L of water at 4°, filtered and shown spectrophotometrically to have a concentration of 32 mg/ml. To 51.5 ml of the glucose oxidase solution was added dropwise 5.15 ml of 0.2 M sodium periodate, the reaction occurring over 25 min. The product was chromatographed on a 2.5×60 cm column of Sephadex G-50 using 2 mM sodium acetate pH 4.5, and the major glucose oxidase peaks pooled to yield 91.5 ml of a solution containing the aldehyde derivative. To the solution was added dropwise 6 ml of 3 M ethylene diamine in 0.2 M sodium carbonate, pH 9.5, and the reaction allowed to proceed for 3 hr. To the mix was then added about 3.9 ml of 10 mg/ml sodium borohydride, the mixture incubated overnight and then chromatographed to remove the sodium borohydride.

EXAMPLE 4

Preparation of HRP-Oxyamine

To 5 ml of 10 mg/ml horse radish peroxidase in 5 mM sodium acetate, pH 4.5 buffer, was added 50 ml 0.2 M sodium periodate and the mixture stirred for 30 min, followed by chromatography on a G-50 Sephadex column, eluting with 2 mM sodium acetate buffer, pH 4.5. The protein fractions were pooled to 29 ml, the mixture cooled to 4° C. and 2.9 ml of 0.2 M 2,2'-oxy-bis-ethylamine in 0.5 M carbonate buffer, pH 9.5 at 4° C. added. The pH of the mixture was adjusted to 9.5 with 1 N sodium hydroxide, stirred for 2 hrs and 3.52 ml of a 4 mg/ml sodium borohydride-water solution added and the mixture allowed to react for 3 hr, followed by chromotography through a Sephadex G-50 column.

The above procedure was repeated using 400 mg of HRP and 3.5 g of 2,2'-oxy-bis-ethylamine. No significant change in enzyme activity was observed between the native amine and the modified amine, which has about four additional amino groups.

In carrying out the assay, 90×8 mm strips were prepared from the sheet prepared in Example 1 and the end of the strip dipped into 1 ml of sample in 0.1 M NaPO4, 0.2 M NaCl, pH7.0 and 1 mg/ml BSA, with a number of samples prepared containing different amounts of theophylline and containing 0.2% Triton DN-65. After 12 min, the strip was then dipped into 5 ml of 0.2 µg/ml HRP-theophylline conjugate, so as to be immersed in the solution and allowed to stand for 10 min. The strip was then removed from the enzyme solution and dipped in a development solution comprising 5 ml of 50 mM glucose and 200 µg/ml 4-chloro-1-naphthol and allowed to stand for 20 min. The distance of the border from the top of the wick was graphed against the samples having differing concentrations of theophylline to provide the following results.

TABLE I

| Theophylline ng/ml | Distance of Border From Strip Top, mm |
|---|---|
| 50 | 66 |
| 100 | 55 |
| 200 | 47 |
| 500 | 42 |

In the next study, the procedure of Example 1 was repeated. The strips employed were 65×8 mm in size. The protocol employed was to dip the end of the strip into 0.5 ml of the solution containing 0.4 µg/ml of the HRP-theophylline conjugate with different samples having varying concentrations of theophylline, each sample containing 0.2% Triton DN-65 and the strip allowed to stand in the sample solution for 6 min. At the end of this time, the strip was immersed in the glucose-(4-chloro-1-naphthol) developer solution to provide the following results.

TABLE II

| Theophylline ng/ml | Distance of Border From Strip Top, mm* |
|---|---|
| 0 | 53 |
| 50 | 46 |
| 100 | 38 |
| 200 | 31 |
| 500 | 26 |

*average of 2 values

In the next example, the paper employed was S.S.589WH, employing a 4% dextran T10 solution as a preservative. The sample solution was 0.5 ml containing varying amounts of theophylline, 0.4 µg/ml of a theophylline-HRP conjugate, having an average of about three theophyllines per enzyme, 0.1% Triton X-100, in the buffer indicated previously. After the sample solution had traversed the immunochromatograph, the immunochromatograph was developed for 10 min with the development solution previously described. It was noted that most of the color which developed was in a narrow band at the border. The following table indicates the results.

TABLE III

| Theophylline ng/ml | Distance of Border From Strip Top, mm* |
|---|---|
| 0 | 26, 25 |
| 50 | 21, 23 |
| 100 | 18, 18 |
| 200 | 15, 12 |
| 500 | 11, 9 |

*two different determinations

It is evident from the above results that a sensitive simple method is provided for quantitatively determining a wide variety of analytes. The protocols are particularly free of nonspecific interference, avoid a plurality of measurements of reagents which introduce errors and are capable of giving a visual result, so as to avoid the need for expensive measuring equipment. In addition, the assay is rapid, so that the result can be carried out in the time a patient stays in a doctor's office. Also, the protocols do not require intermediate washing steps, which is particularly important where relatively untrained personnel are to carry out the determination. Washing steps, where required have been a continuous source of substantial error.

Although the foregoing invention has been described in some detail by way of illustration and example for purposes of clarity of understanding, it will be obvious that certain changes and modifications may be practices within the scope of the appended claims.

What is claimed is:

1. A method for determining the presence of an analyte in a sample suspected of containing said analyte, said method employing:
   (A) an immunochromatograph having a porous support permitting solvent travel and a plurality of a specific binding pair member ("mip") and a second enzyme, which mip and second enzyme are non-diffusively and uniformly bound to said support and extend a distance away from a first end of said support to define an immunosorbing zone; and
   (B) a labeled mip, where said labeled mip is chosen to bind to said immunosorbing zone in relation to the portion of said immunosorbing zone in which said analyte is bound to define a border related to the amount of analyte present in said sample, said label being an enzyme which is part of a signal producing system including a first enzyme, wherein said first and second enzymes are related by the substrate of one being the product of the other, and which system produces a detectable signal of electromagnetic radiation defining said border;
   said method comprising:
   contacting said immunochromatograph: (1) at said first end with sample containing solvent for a time sufficient for at least a portion of said solvent to traverse said immunosorbing zone; and (2) with labeled mip containing solvent, where said labeled mip binds in said immunosorbing zone in relation to the analyte bound in said immunosorbing zone, and where steps (1) and (2) are concurrent or consecutive; and
   determining the border defined by said labeled mip by means of said signal producing system, by contacting said immunosorbing zone with the remaining members of said signal producing system, where the position of the border relates to the amount of analyte present in said sample.

2. A method according to claim 1, wherein at least one enzyme is an oxidoreductase.

3. A method according to any of claims 1, or 2, wherein said labeled mip and said sample are included in the same solvent.

4. A method according to claim 3, wherein said labeled mip traverses said immunosorbing zone at a slower rate than said analyte, so as to concentrate at about a border between an analyte containing region and an analyte free region.

5. A method according to claim 3, where said determining includes the step of immersing said immunosorbing zone in a solution containing an enzyme substrate which is enzymatically transformed to a product capable of detection by electromagnetic radiation.

6. A method according to claim 5, wherein said product absorbs light in the visible range.

7. A method for determining the presence of an analyte in a sample suspected of containing said analyte, said method employing:
   (A) an immunochromatograph having a porous support permitting solvent travel and non-diffusively and uniformly bound to said porous support a plurality of a specific binding pair member ("mip") and a plurality of a second enzyme, extending a distance away from the first end of said support to define an immunosorbing zone; and
   (B) a first enzyme labeled mip, where said first and second enzymes are related by the product of one enzyme being the substrate of the other enzyme and said labeled mip is chosen to bind to said immunosorbing zone in relation to the portion of said immunosorbing zone in which said analyte is bound to define a border related to the amount of analyte, and where said enzymes and a substrate which produces a dye which binds to said support are members of a signal producing system;
   said method comprising:
   contacting said immunochromatograph at said first end with a solution containing sample and first enzyme labeled mip for a time sufficient for at least a portion of said solution to traverse said immunosorbing zone, where said enzyme labeled mip binds in said immunosorbing zone in relation to the analyte bound in said immunosorbing zone; and
   containing said immunosorbing zone in a substrate containing solution resulting in depositing of said dye in the environs of said second enzyme on said support defining a region in which analyte is bound,
   wherein the distance the border of said region is from one end of said immunochromatograph is related to the amount of analyte in said sample.

8. A method according to claim 7, wherein said dye is deposited primarily at said border.

9. A method according to claim 7, wherein said dye is deposited throughout said region in which analyte is bound.

10. A method according to claim 7, wherein said first and second enzymes are oxidoreductases.

11. A method according to claim 10, wherein said first enzyme is a peroxidase and said second enzyme produces hydrogen peroxide.

12. A method according to claim 11, wherein said second enzyme is an oxidase.

* * * * *